United States Patent [19]

Vijay et al.

[11] 4,387,091

[45] Jun. 7, 1983

[54] NON-ALLERGENIC PROTECTIVE ANTIGENS FROM MOLDS AND PROCESS FOR PREPARATION THEREOF

[75] Inventors: Hari M. Vijay; Noel M. Young, both of Ottawa, Canada; I. Leonard Bernstein, Cincinnati, Ohio

[73] Assignee: Canadian Patents & Development Limited, Ottawa, Canada

[21] Appl. No.: 240,759

[22] Filed: Mar. 5, 1981

[51] Int. Cl.³ .................................. A61K 39/00
[52] U.S. Cl. ........................................... 424/88
[58] Field of Search ................................ 424/88, 91

[56] References Cited

U.S. PATENT DOCUMENTS 4,138,479  2/1979  Truscheit et al. ................... 424/88

OTHER PUBLICATIONS

International Archives of Allergy and Applied Immunology 60: (1979) pp. 229-239-H. M. Vijay et al.
International Archives of Allergy and Applied Immunology 65: (1981) pp. 410-416-H. M. Vijay et al.

Primary Examiner—Sam Rosen
Attorney, Agent, or Firm—Alan A. Thomson

[57] ABSTRACT

Certain isolated fractions, extracted from allergy-causing molds, have been found to be antigenic but non-allergenic, and are able to decrease substantially or prevent the susceptibility to mold allergens of allergic individuals. The antigenic non-allergenic fractions contain protein and carbohydrate and have molecular weights which have been found to vary with the mold source. Increased polyvalent protection can be realized by combining fractions from different molds, e.g. Alternaria with Hormodendrum or Helminthosporium. The extracts are administered parenterally, preferably subcutaneously in isotonic saline.

21 Claims, 4 Drawing Figures

NON-ALLERGENIC PROTECTIVE ANTIGENS FROM MOLDS AND PROCESS FOR PREPARATION THEREOF

FIELD OF INVENTION

Allergic reactions to molds can be decreased or prevented by administration of a fraction extracted from molds. A particular fraction has been found to be antigenic and immunogenic but not allergenic. Similar fractions can be isolated from the various types of molds. These fractions have been found related to the major allergen but with the important difference that while they are able to induce IgG antibodies (antigenic and immunogenic), they do not induce IgE antibodies nor elicit anaphylactic reaction (i.e. are non-allergenic). These fractions are capable of inhibiting the binding of specific IgE antibodies obtained from patients allergic to molds in radio-allergosorbent (RAST) assays. Therefore, these fractions possess appropriate characteristics required for a therapeutic agent capable of desensitizing mold-allergic patients with safety. As an example, preparation and biological testing of a specific fraction (AT-G3, and subfraction G3D5) of *Alternaria tenuis* is described in detail.

DESCRIPTION OF PRIOR ART

Allergic reactions arise from the interaction of a minor class of antibodies, known as IgE, with particular components (allergens) of the material in which a patient is sensitive. While anti-histamines, etc., can control immediate symptoms, the major long-range curative therapy is to administer extracts containing the allergens to the patient. The aim of this "desensitization" approach is to induce antibodies of the major class, IgG, which can then compete with the IgE antibodies for the allergen, thereby reducing IgE-allergen interaction.

These desensitizing extracts are at present crude mixtures of which only a part is the allergen(s). Naturally, administration of such extracts presents the risk of inducing generalized systemic reactions since the actual active material to which the patient is sensitive is being used; and hence only small amounts can be given. Even these small amounts can induce some initial allergic reactions. The benefit relates directly to the total dose of allergen injected. Improvements in desensitizing preparations are therefore being sought.

A highly desirable property of an improved desensitizing preparation would be that it cause the production of the desired IgG type of antibody without interaction with the IgE system, thus reducing the risk of allergic response upon administration of the preparation. The presently published approaches are to purify the allergen from an extract and then chemically modify it to diminish its allergenic potency (IgE reaction) while retaining its antigenic potency (IgG production). Examples of the modifying methods are: polymerization of ragweed antigen E and whole ragweed with glutaraldehyde (R. Patterson et al, 1973, J. Immunol. 110, 1413–1418, and E. Bacel et al, 1978, J. Allergy and Clin. Immunol. 62, 289–294); and treatment of rye grass (Z. H. Haddad et al, 1973, J. Allergy and Clin. Immunol. 49, 197–209) and mixed grass allergens (D. G. Marsh et al, 1972, Immunology 22, 1013–1028) with formaldehyde. These modified allergens have been reported to display a reduced capacity of allergenic activity but retain the antigenic properties characteristic of the native molecule. Recently, ragweed and ovalbumin allergens have been modified with polyethylene glycol or polyvinyl alcohol (W. Y. Lee and A. H. Sehon, 1978, Int. Archs. Allergy, 56, 193–206, and 1979, Immunology Letters, 1, 31–37). These conjugated products have been reported to be non-immunogenic, non-allergenic and non-antigenic. They suppressed the specific IgE antibody response. However, these chemically-modified allergen products have not been evaluated for their stability and toxicological properties. Moreover, a limitation of these processes is that they require fairly pure allergens to start with. Obviously, there would be risks associated with manufacture of the highly pure and hence, very potent allergen. Allergens (pollens) polymerized with glutaraldehyde are not completely devoid of allergenic activity although they display reduced activity (100× less allergenic) compared to native allergens. Allergens coupled with polyethylene glycol or polyvinyl alcohol are also non-immunogenic; hence, these modified products may not be able to produce appropriate IgG antibodies which are vital as clinical relief is correlated with increased levels of appropriate serum IgG antibodies.

There have been reports of "inhibitory" substances present in allergenic extracts of various pollens (N. A. Attallah and A. H. Sehon, 1969, Immunochemistry, 6, 609–619; A. Malley and R. L. Harris Jr., 1969, J. Immunol., 99, 825; and A. Malley et al, 1975, J. Allergy and Clin. Immunol., 56, 282–290). These were able to block interaction of IgE with allergen but were not reported to be able to induce IgG antibodies. In technical terms, they were haptens not antigens. They are, therefore, of much less therapeutic potential, since they would have to be administered continuously to effect any disruption of the IgE-allergen interaction.

Rye grass pollen allergens have been reported to contain a material which is very weakly active in monkey passive cutaneous anaphylaxis (N. R. Lynch and K. J. Turner, 1974, Int. Archs. Allergy, 47, 818–828). The activity of this fraction was comparable to that of allergenic fractions of rye grass when tested by RAST inhibition. This material was not tested for its ability to produce IgG antibodies.

Recently, reports have appeared on the isolation of Alternaria allergens. J. W. Yunginger and R. T. Jones, 1978, Abstract 1561, Fed. Proc. 37, 1553, have fractionated an extract of *Alternaria tenuis* and found fractions which appeared to contain the major allergens of this species. W. R. Solomon et al, 1980, Abstract 213, Annual Meeting, Amer. Acad. of Allergy, compared the allergenic properties of Alternaria spore, mycelial and "metabolic" extracts. Also we have found previously that certain extract fractions (high molecular weight non-dialyzable fractions) contained the major allergenic activity. However, none of these prior art reports described a non-allergenic but antigenic and protective fraction.

PRESENT INVENTION

In the case of allergenic molds, we have found that there are present naturally, in certain extract fractions of molds, substances which are related in the allergens but with important differences that while they can induce IgG antibodies, they do not cause allergic reactions. They are incapable of inducing IgE antibodies nor of eliciting skin reactions against antibodies to major allergens. They therefore have the desired properties of a therapeutic agent as described above, in their natural form without chemical modification. Furthermore, they can be purified with much less risk than for allergen itself. For example, Alternaria sp. have been derived frequently in routine atmospheric sampling in many countries, are commonly found in soil, and are known to be important causes of bronchospasm in a significant number of patients with bronchial asthma. Selected extract fractions of such molds have been found to have the desired properties for an immunogenic therapeutic against mold allergies.

SUMMARY OF THE INVENTION

The invention includes a method of decreasing or preventing allergic reactions in animals allergic to molds, comprising administering parenterally to an animal allergic to molds, in an amount sufficient to decrease or prevent susceptibility of said animal to mold allergens, a protein- and carbohydrate-containing antigenic fraction extracted from mold causing such allergic reactions, said fraction being characterized by being non-allergenic, and being obtained by steps comprising:

(a) defatting mold solids, (b) extracting the defatted solids with an aqueous solution of pH about 7–8, (c) dialyzing the extract solution to remove solute of less than about 10,000 MW, (d) fractionating the extract by the equivalent of gel filtration on a medium operative to fractionate in the MW range 10,000–100,000, and (e) recovering the fraction showing RAST potency and lacking allergenicity, and capable of inducing IgG antibodies. The active fraction may be further purified by additional steps comprising, e.g. (f) ion exchange chromatography, and optionally (g) dialysis against water.

It is advantageous, for a more polyvalent protective effect, to administer the similar fractions from at least two molds, preferably ones whose antigenic non-allergenic fraction is non- or only weakly-cross-reactive with the other.

The invention includes the most active antigenic Alternaria subfraction characterized by being non-allergenic, containing protein and carbohydrate, having a molecular weight (MW) of the order of about 25,000 and being obtained by steps comprising:

(a) defatting Alternaria mold solids, (b) extracting the defatted solids with an aqueous solution of pH about 7–8, (c) dialyzing the extract solution to remove solute of less than about 10,000 MW, (d) fractionating the extract by the equivalent of gel filtration on a medium operative to fractionate in the MW range, 10,000–50,000, (e) recovering the fraction encompassing the equivalent of the G3 region in FIG. 1, and (f) subjecting said recovered fraction from (e) to subfractionation by ion exchange chromatography, and recovering the subfraction encompassing the equivalent of the G3D5 region in FIG. 2C.

The invention also includes the antigenic Hormodendrum fraction characterized by being non-allergenic, containing protein and carbohydrate, and being obtained by steps comprising:

(a) defatting Hormodendrum mold solids, (b) extracting the defatted solids with an aqueous solution of pH about 7–8, (c) dialyzing the extract solution to remove solute of less than about 10,000 MW, (d) fractionating the extract by the equivalent of gel filtration on a medium operative to fractionate in the MW range about 10,000–100,000, and (e) recovering the fraction eluting between bovine serum albumin MW 68,000 and carbonic anhydrase MW 30,000, which has antigenic and immunogenic properties including RAST potency, and is lacking in allergenicity.

The invention further includes a pharmaceutical composition giving polyvalent protection against allergic reactions in animals allergic to molds, comprising at least two antigenic fractions isolated from different allergy-causing molds and which are substantially non-cross-reactive, each fraction being characterized by being non-allergenic, containing protein and carbohydrate, and being obtained by steps comprising:

(a) defatting mold solids, (b) extracting the defatted solids with an aqueous solution of pH about 7–8, (c) dialyzing the extract solution to remove solute of less than about 10,000 MW, (d) fractionating the extract by the equivalent of gel filtration on a medium operative to fractionate in the MW range about 10,000–100,000, and (e) recovering the fraction showing RAST potency and lacking allergenicity, and capable of inducing IgG antibodies. When used herein, the word "animals" is meant to include humans.

DETAILED DESCRIPTION AND PREFERRED EMBODIMENTS

The molds may be any type known to cause allergic reactions and usually are selected from species of Alternaria, Hormodendrum, Helminthosporium, Aspergillus and Penicillium. Common species known to cause allergic reactions include *Alternia tenius, A. solani, Aspergillus fumigatus,* Hormodendrum (Cladosporium), and *Penicillium notatum.* We have observed strong cross-reactivity when using the antigenic fraction from one of *A. tenuis, A. solani* or *Aspergillus fumigatus* and challenging with antigens of either of the other two species. Only weak cross-reactions with Alternaria were obtained on challenging with antigens from Hormodendrum or Helminthosporium. Thus for more polyvalent protection it is desirable to combine antigenic fractions (or administer both separately) from e.g. Alternaria with fractions from Hormodendrum, Helminthosporium or other genus which is non- or only weakly-cross-reactive therewith.

The route of administration is any parenteral route known for such materials used in treating allergies in humans or other animals allergic to molds. These include subcutaneously, intradermally, or intramuscularly. The preferred route is subcutaneously. Since the fractions are non-allergenic, administration may also be in the form of a spray to the nose or mouth for transmucosal effect.

Figures 2A, 2B:
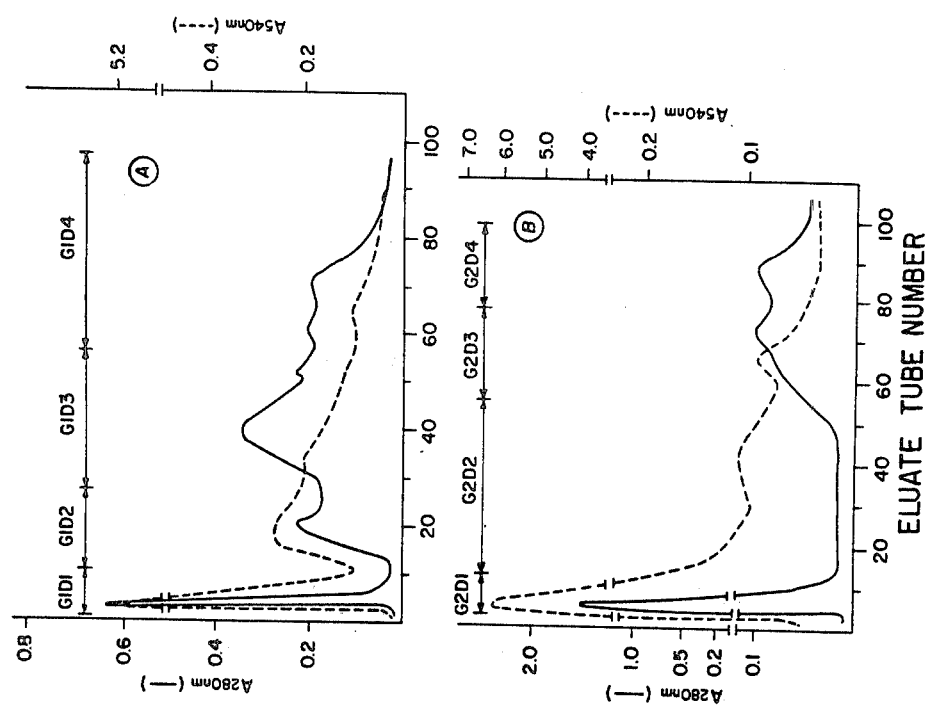
FIGS. 2A, 2B and 2C are graphs plotting eluate tube number versus absorbance at 280 nm and carbohydrate content (as in FIG. 1) on ion-exchange chromatography of fractions G1 (FIG. 2A) and G2 (FIG. 2B) fractions of *A. tenuis* on DEAE-cellulose. Successive tubes (5 ml each) were pooled into subfractions as indicated at G1D1, etc. In the case of G3 (FIG. 2C), tubes of 6.25 ml were collected and combined into eight pools on the basis of immuno-diffusion tests. The arrows at the bottom indicate regions where positive immuno-diffusion tests were obtained.
Figure 2C:
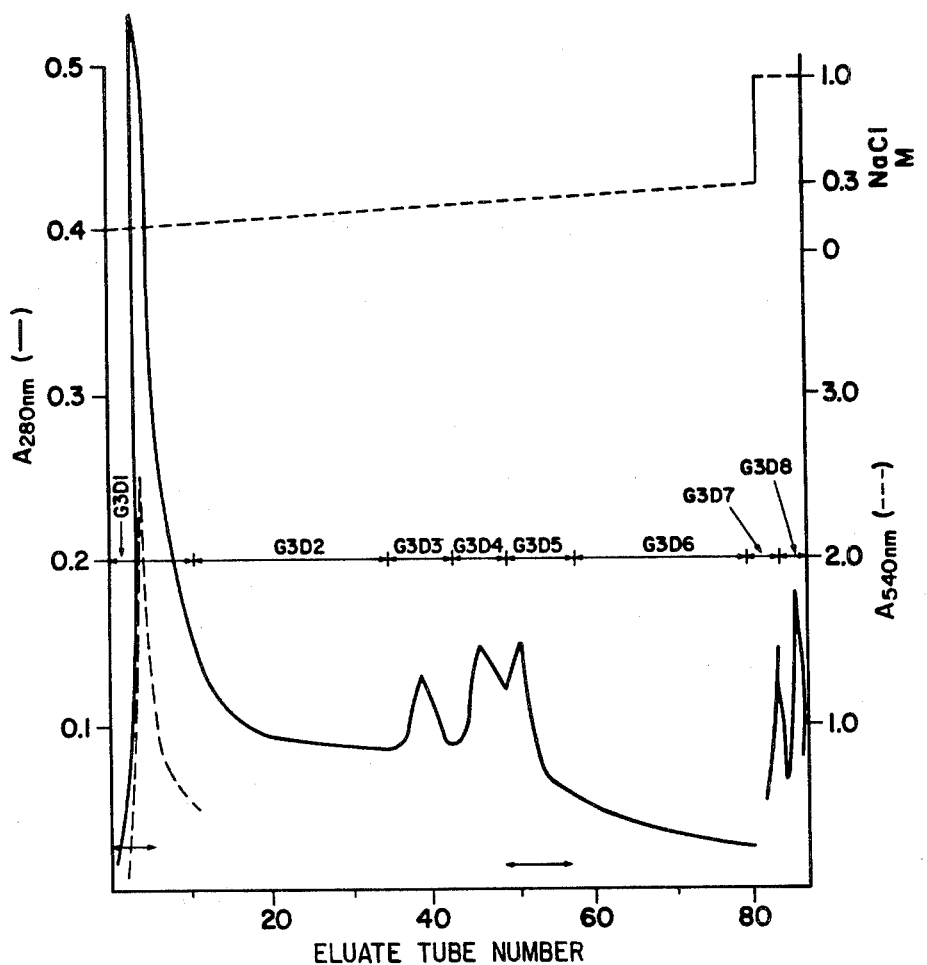

The dosage may be any effective amount tolerated by the individual. Usually the dose for an average human will be an effective amount within the approximate range of from about 0.02 up to about 20 micrograms of total protein. For antigenic fractions which are about 20% protein, each total dose usually will range from about 0.1 to about 100 micrograms. A series of doses of increasing amounts within said range is commonly given over several days or weeks. In the case of rush desensitization, a single larger dose may be administered. Booster doses may be given at longer intervals to maintain the level of protection or immunity desired. The active fractions are normally stored in the lyophilized state and are quite stable in this form. Potency can be checked by RAST inhibition and a standardized potency maintained.

The antigenic fraction may be administered in any suitable pharmaceutical carrier known for parenteral and spray application. For injection isotonic saline, aqueous dextrose and glycols may be used as liquid carriers with isotonic saline preferred. Sustained release formulations are desirable. Liposome envelopes may be used to enclose the active material. Adjuvants, especially those giving a sustained release of activity have been found desirable. Suitable adjuvants include aluminum hydroxide or sulfate, an alum, an alginate, and others known for such purpose. Precipitated alum is a preferred adjuvant with these antigenic, non-allergenic fractions.

The antigenic, non-allergenic fractions contain both protein and carbohydrate, and are obtained by at least one of gel filtration or ion exchange chromatography. In the case of AT-G3 described below, the protein content is about 20%, the carbohydrate content about 80% and the total nitrogen about 3.3%. Active fractions have also been obtained from *A. solani* and from Hormodendrum. The MW has been found to vary depending on the mold source.

It will be evident to one skilled in the art that minor variations may be made in the extraction and fractionating steps while obtaining equivalent results. In particular, any equivalent gel filtration or ion exchange chromatographic fractionation may be carried out at (d) and (f) as long as the same fraction is isolated and recovered. Various operative gel filtration media and ion exchange chromatographic substrates are known to be able to separate proteins and carbohydrates in the MW range about 10,000–100,000, and the ones used in the examples are not critical.

We describe in the examples following (which are illustrative only) the preparation and properties of a fraction AT-G3, and subfraction G3D5, which is (a) capable of IgG formation in rabbits, (b) the most potent fraction by RAST inhibition, i.e. inhibits the binding of human specific IgE antibodies to *A. tenuis* allergens, (c) incapable of inducing reaginic antibodies in rats or eliciting skin reaction against antibodies to *A. tenuis* allergens, and (e) shares common antigenic determinants to a large extent with major and minor allergens of Alternaria as shown below by various immunological studies. This fraction is capable of desensitizing *A. tenuis* allergic patients without unleashing anaphylaxis or enhancing the initial titer of specific IgE antibodies. Purification of an active subfraction AT-G3D5 is also described. The similar fraction found active from Hormodendrum also is described. Similar fractions from other molds would be prepared analogously.

A. PREPARATION OF THE ANTIGENS

Example A1

Fifty grams of *A. tenuis* powder were defatted four times with 250 ml of acetone at room temperature. The resulting defatted material (38.0 g) was extracted twice with 190 ml of 0.05 M tris(hydroxymethyl)-aminomethane buffer, pH 7.8, containing 0.15 M NaCl (Tris-saline) and stirred magnetically for 48 h at 4° C. The suspension was centrifuged at 1000 g at 4° C. for 30 min. The supernatant was centrifuged at 30,000 g at 4° C. for 20 min to remove trace suspended particles. The resulting supernatant which we term *A. tenuis* crude extract (AT-CE) was concentrated by ultrafiltration with an Amicon [trademark] UM-2 membrane (Amicon Corporation, Lexington, Mass.). The concentrated AT-CE was dialyzed for 48 h at 4° C. against three changes of Tris-saline buffer, using dialysis tubing with an approximate 10,000 MW cut-off. The non-dialyzable material (AT-ND) was further dialyzed exhaustively against water and freeze-dried. Extraction of 38.0 g defatted *A. tenuis* yielded 1.8 g of water-soluble AT-ND material.

500 mg of AT-ND product were dissolved in 20 ml of 0.02 M phosphate buffer, pH 7.0 and subjected to gel filtration on a column (5×85 cm) of cross-linked dextran Sephadex G-100 [Trademark-Pharmacia Laboratories, Montreal, Quebec] at 4° C. Carbohydrate content was assayed by the orcinol/sulphuric acid method using glucose as a standard. The column was calibrated with bovine serum albumin (MW, 68,000), carbonic anhydrase (MW, 29,000), and lysozyme (MW, 14,000). Gel filtration of 500 mg of AT-ND resulted in three fractions, AT-G1, AT-G2 and AT-G3 (163 mg) on the basis of 280 nm absorption and carbohydrate analyses (see FIG. 1).

Example A2—Ion-Exchange Chromatography

The fractions of AT-ND allergens obtained from the Sephadex G-100 gel-filtration were further purified by ion-exchange chromatography on DEAE-cellulose (Whatman DE-52 [Trademark], Mandel Scientific Ltd., Montreal, Quebec). Fraction G1 was concentrated to 20 ml and absorbed onto a column (1.6×25 cm) of DEAE-cellulose equilibrated with 0.02 M phosphate buffer, pH 7.0 at 4° C. After washing the column with the same buffer, a linear gradient made from 250 ml of 0.02 M phosphate buffer, pH 7.0, and 250 ml of phosphate buffer containing 0.3 M NaCl was used to elute the material from the column. The eluted material was combined into four fractions, G1D1, G1D2, G1D3, and G1D4 which were dialyzed against water and freeze-dried.

Fraction G2 from the Sephadex G-100 fractionation step was similarly subfractionated by DEAE-cellulose chromatography.

In case of fraction G3, the eluates were tested by immunodiffusion in gel with rabbit antisera to AT-G3.

The eluates were combined into eight fractions (AT-G3D1, G3D2, G3D3, G3D4, G3D5, G3D6, G3D7 and G3D8) which were dialyzed against water and freeze-dried. (See FIGS. 2A, 2B and 2C, showing ion-exchange chromatography of fractions AT-G1, AT-G2, and AT-G3, respectively). The G3D5 subfraction had a MW of the order of about 25,000 as determined by high performance liquid chromatography.

B. IMMUNOLOGICAL STUDIES

Example B1—Direct RAST and RAST Inhibition Studies

Allergenic potencies of AT-CE and its fractions obtained by Sephadex G-100 and DEAE-cellulose separations were tested in vitro by direct RAST and RAST inhibition techniques.

Filter paper discs activated with CNBr were coupled with AT-CE at concentrations ranging from 1 μg to 2 mg/disc. Direct RAST assay was performed using reference sera and $^{125}I$ anti-human IgE. A number of sera obtained from patients allergic to molds were screened by direct RAST using discs coupled with AT-CE. Equal amounts of 5 sera which gave 3+ reaction in RAST were pooled together. None of these patients had been treated by hyposensitization therapy with *A. tenuis* allergens. The RAST assay was performed with the pooled serum using discs coupled with AT-CE or fractions obtained from it (100 μg/disc). The percent of total count bound by normal serum control was subtracted from all of the tests. Results were expressed as the percentage of total radioactive counts bound to the discs.

RAST inhibition assays were performed in essentially the same way as the direct RAST with the exception that the pooled serum and solid phase allergen (disc coupled with 100 g of AT-CE) were incubated in the presence of inhibitor, i.e. AT-CE and its fractions, at concentrations ranging from 0.1 μg to 100 μg. The degree of inhibition of RAST reactivity was obtained by subtracting the mean percentage (average of duplicates) of residual radioactivity of the absorbed samples from 100%, i.e. the value given by a control sample containing the pooled serum alone but diluted to comparable volume with the buffer used in the above assay. Means values of individual experiments were plotted on semilogarithmic paper from which results could be expressed as the amounts of absorbing allergen causing 50% inhibition of RAST.

It was consistently found that in both RAST and RAST inhibition assay, AT-G3 was the most potent fraction followed by AT-G2D3 and AT-G2D4 (see Table 1).

In the RAST tests, in which AT-CE was coupled to the discs, all reaginic activity could be inhibited by G2D3, G2D4 and G3. This indicates that the antigenic determinants being recognized by the patient's IgE antibodies are relatively few in number and that all determinants are present in each of the three fractions.

Example B2—Passive Cutaneous Anaphylaxis (PCA) Performed on Rat

Eleven groups, each consisting of male inbred Wister Furth rats weighing 225–250 g (Microbiological Associates, Bethesda, Md.) were immunized. Animals in each group were given a single intraperitoneal injection of 1.0 ml containing 200 μg of one of the eleven fractions (AT-CE, AT-ND, AT-G1D1, AT-G1D2, AT-G1D3, AT-G1D4, AT-G2D1, AT-G2D2, AT-G2D3, AT-G2D4, and AT-G3) precipitated with 30 mg of aluminum hydroxide (Amphojel [Trademark], Wyeth Ltd., Toronto, Ontario, Canada).

TABLE I

Potency of *A. tenuis* fractions in direct RAST and RAST inhibition assays

| A. tenuis fraction | yield* (mg) | RAST** percent counts bound | Amount required for 50% RAST inhibition (μg) |
|---|---|---|---|
| AT-CE | — | 29.4 | 2.2 |
| AT-ND | 500 | 31.1 | 1.4 |
| AT-G1D1 | 34.4 | 20.6 | >500 |
| AT-G1D2 | 7.3 | 21.5 | 168.0 |
| AT-G1D3 | 23.8 | 23.8 | 5.2 |
| AT-G1D4 | 16.7 | 27.9 | 3.0 |
| AT-G2D1 | 38.4 | 19.5 | 112.0 |
| AT-G2D2 | 7.3 | 15.8 | 100.0 |
| AT-G2D3 | 14.0 | 27.9 | 1.2 |
| AT-G2D4 | 40.2 | 28.9 | 1.0 |
| AT-G3 | 163.0 | 31.4 | 0.8 |

*From 500 mg of AT-ND.
**Total count in 50 μl (8 ng) of 125I anti-human IgE was 24,781, using discs coupled with AT-CE.

The animals were given Halothane [Trademark] anaesthesia and bled by cardiac puncture at days 11, 14, 18, 21 and 24 postimmunization. The serum samples were stored at −70° C. until used in PCA reactions.

The level of specific IgE antibodies in these antisera was determined by the PCA test using a sensitization period of 24 h. Briefly, 0.1 ml quantities of various dilutions of test sera were injected intradermally into the skin of two different rats. The animals were subsequently challenged intravenously with either 2 mg of AT-ND or 1 mg of the immunizing antigen to 0.5 ml saline, mixed with 0.5 ml of 2% Evens blue dye. The skin reactions were examined after 30 min. Duplicate antibody titers were expressed as the reciprocal of the highest dilution giving a blueing diameter greater than 5 mm. Heat-stable homocytotropic antibody (IgGa) was measured by performing 2 and 4 h PCA tests with the antisera which had been heated at 56° C. for 4 h. The results of this study are shown in Table II.

It was found that the reaginic antibodies of highest response, i.e. PCA titer of 32 to 64, were present in the sera of rats immunized with either G2D3 or G2D4 fractions. Moreover, 100% rats immunized with fraction G3 failed to elicit PCA reactions. Out of nine rats immunized with G3, only one rat showed a positive PCA reaction and that of a low titer. In further similar tests, 24 other rats were negative in PCA tests. These results were further confirmed by performing (a) PCA reactions in which the homologous antigen was used as a challenging antigen and (b) PCA reactions in which AT-ND was used as a sensitizing antigen and AT-G3 as the challenging antigen. The results are summarized in Table III. The antisera to G2D3 and G2D4 on challenge with their homologous antigen gave PCA titers of 64 which was similar to that obtained with AT-ND as a challenging antigen. On the other hand, sera from the rats immunized with AT-G3 even on challenge with homologous antigen failed to show any positive PCA reaction. Serum from one positive rat gave PCA titer of only 2 which may be compared with a titer of 8 when AT-ND was the challenging antigen.

TABLE II

Mean* homocytotropic (IgE) antibody titers in rats immunized with various fractions of *A. tenuis*. PCA titers on challenge with AT-ND fraction

| Immunizing antigen | Reciprocal PCA titers Days after immunization | | | | |
|---|---|---|---|---|---|
| | 11 | 14 | 18 | 21 | 24 |
| AT-CE | 8(8/10) | 16(1/10) | 0(0/9) | 2(1/9) | 0(0/9) |
| AT-ND | 16(13/18) | 4(4/18) | 8(2/18) | 2(2/18) | 0(0/18) |
| AT-G1D1 | 0(0/9) | 0(0/9) | 0(0/9) | 0(0/9) | 0(0/9) |
| AT-G1D2 | 0(0/9) | 2(1/9) | 0(0/8) | 0(0/9) | 0(0/7) |
| AT-G1D3 | 8(8/9) | 0(0/8) | 0(0/8) | 0(0/8) | 0(0/8) |
| AT-D1D4 | 4(3/9) | 8(9/9) | 8(9/9) | 2(2/9) | 2(3/9) |
| AT-G2D1 | 2(2/9) | 8(1/9) | 4(1/9) | 2(2/9) | 2(1/9) |
| AT-G2D2 | 16(4/5) | 16(4/5) | 8(3/5) | 0(0/5) | 0(0/3) |
| AT-G2D3 | 32(9/9) | 32(9/9) | 8(9/9) | 0(0/9) | 2(1/9) |
| AT-G2D4 | 64(9/9) | 64(9/9) | 32(9/9) | 8(8/9) | 2(3/9) |
| AT-G3 | 0(0/9) | 8(1/9) | 0(0/9) | 0(0/9) | 0(0/9) |

*In each group, positive sera were pooled.
( ): Number of rats showing positive PCA reaction.

TABLE III

Mean* homocytotropic (IgE) antibody titers in rats immunized with various fractions of *A. tenuis*. PCA titers on challenge with homologous antigen

| Immunizing and challenging antigen | Day of bleeding | No of rats positive to AT-ND Challenge | Reciprocal PCA titer on challenge with | |
|---|---|---|---|---|
| | | | homologous antigen | AT-ND |
| AT-CE | 11 | 8/10 | 16 | 8 |
| AT-ND | 11 | 13/18 | 16 | 16 |
| AT-G1D1 | 11 | 0/9 | 0 | 0 |
| AT-G1D2 | 14 | 1/9 | 4 | 2 |
| AT-G1D3 | 11 | 8/9 | 32 | 8 |
| AT-G1D4 | 14 | 9/9 | 64 | 8 |
| AT-G2D2 | 11 | 4/5 | 4 | 16 |
| AT-G2D3 | 11 | 9/9 | 64 | 32 |
| AT-G2D4 | 11 | 9/9 | 64 | 64 |
| AT-G3 | 14 | 1/9 | 2 | 8 |
| AT-ND (Immunizing antigen), AT-G3 (challenging antigen) | 11 | 13/18 | 0 | 16 |

*In each group, positive sera were pooled.

It should be noted that fraction G3 also did not elicit skin reactions in rats sensitized with reagins against AT-ND. These results suggest that G3, whose molecular weight is of the order of 25,000 and which appeared to be the most potent fraction in RAST assays was neither capable of inducing reaginic antibodies in rats nor eliciting skin reactions in rats sensitized with reagins against AT-ND. On the other hand, G2D3 and G2D4, which have molecular weights of the order of 30,000–40,000 and are the most potent fractions after AT-G3 in RAST assays, exerted the greatest allergenic activity (IgE antibody response) in vivo. None of the antisera heated at 56° C. for 4 h elicited any PCA reactions at 2 and 4 h indicating a lack of IgGa antibody.

Example B3—Antisera Preparation

Antisera were prepared to AT-CE, AT-ND and AT-G3 fractions of *A. tenuis* extracts by immunizing New Zealand white rabbits (2 to 3 lbs) by subcutaneous injection into four foot pads, of an emulsion prepared from 1 ml of saline, containing 2 mg of Alternaria, extract, and 1 ml complete Freund's adjuvant (Difco Laboratories, Detroit, Mich). Two weeks later, the animals received the same dose of antigen in 1 ml of emulsion. Thereafter for seven weeks, trial bleeding and booster shots were carried out at weekly intervals.

IMMUNODIFFUSION

Immunodiffusion was performed in 1% agar prepared in 0.05 M barbitol buffer, pH 8.2, containing 1% polyethyleneglycol (MW, 6000), for periods of 48–72 h at 4° C. (see H. M. Vijay et al, 1979, Int. Arch. Allerg. 60, 229). Samples of 50 μl of 2 mg/ml solution of the antigens were applied to the well. (The antigenic composition of fractions in gel diffusion demonstrated that antiserum against AT-CE when tested against AT-ND and AT-G3 gave three precipitin bands against AT-ND [two of them appeared to be identical to those of AT-G3].) Serum from rabbit 284 immunized with AT-G3 gave only one precipitin band against AT-G3 and G2D3 and G2D4 indicating common antigenic determinants. Serum from rabbit 282 immunized with AT-G3 gave two precipitin bands with AT-G3 which were also given by G2D3 and G2D4 fractions. The pattern of one line was similar to that given by rabbit 284. These results show that AT-G3 though non-allergenic (being incapable of inducing IgE antibody in rats) is a good antigen for production of IgG antibodies in rabbits.

Example B4—Immunodiffusion & RAST Studies of AT-G3 Fractions

RAST inhibition studies (see Table IV) using discs coupled with AT-CE indicated that fraction G3D5 contained the most active material, though its specific activity was only of the level of the starting material G3. This fraction also was positive in immuno-diffusion tests with both antisera (rabbits 282 and 284). These results indicate that G3D5 is the antigen of major importance but lost some activity during the further purification or freeze-drying. Fraction G3D1, while the largest fraction by weight, and containing carbohydrate, gave virtually no RAST inhibition and reacted with only one antiserum, No. 282.

Example B5—Passive Cutaneous Anaphylaxis (PCA) Performed on Guinea Pig

In order to compare PCA activity of rabbit anti-AT-G3 with rabbit anti-AT-ND (the mother antigen), intradermal injections of 0.1 ml quantities of test serum serially diluted in saline were made into the back of the freshly shaved male Hartly Strain albino Guinea pigs (250–350 g). All tests were done in duplicate animals. After 4 to 5 hours, the animals were injected intravenously with AT-ND extract (2 mg in 0.5 ml saline) mixed with 1.5 ml of B 2% Evans blue dye. The skin reactions were examined after 20 minutes. The antibody titers were determined in duplicate and are expressed as the reciprocal of the highest dilutions giving a diameter greater than 5 mm in blueing reaction.

TABLE IV

Properties of AT-G3 fractions

| AT-G3 fractions | Yield* (mg) | Amount required for 50% RAST inhibition (μg) | Immunodiffusion** | |
|---|---|---|---|---|
| | | | Rabbit No 282 | Rabbit No 284 |
| AT-G3 | 80.6 | 0.8 | +ve | +ve |
| AT-G3D1 | 42.1 | >500 | +ve | −ve |
| AT-G3D2 | 6.16 | 3.8 | −ve | −ve |
| AT-G3D3 | 8.88 | 13.1 | −ve | −ve |
| AT-G3D4 | 1.0 | 2.5 | −ve | −ve |
| AT-G3D5 | 0.36 | 0.7 | +ve | +ve |
| AT-G3D6 | 1.19 | 1.4 | −ve | −ve |
| AT-G3D7 | 7.4 | 113.3 | −ve | −ve |

TABLE IV-continued

Properties of AT-G3 fractions

| AT-G3 fractions | Yield* (mg) | Amount required for 50% RAST inhibition (μg) | Immunodiffusion** Rabbit No 282 | Rabbit No 284 |
|---|---|---|---|---|
| AT-G3D8 | 7.2 | 500.0 | −ve | −ve |

*From 80.6 mg of AT-G3.
**Tests of anti-G3 antiserum against AT-G3 fractions obtained on DEAE-cellulose.

TABLE V

PCA titers of rabbit antiserum to AT-ND and AT-G3 using AT-ND as a challenging antigen.

| Antiserum tested | PCA titer | Diameter (mm) |
|---|---|---|
| Untreated At-ND antiserum | 2048 | 7 × 5 |
| Untreated AT-G3 antiserum | 1024 | 6 × 5 |
| AT-ND antiserum absorbed with AT-G3 | 256 | 5 × 5 |

In another embodiment, the ability of AT-G3 fraction to inhibit PCA activity of AT-ND antibody was examined. Volumes of 0.2 ml of AT-ND antiserum were incubated with 2 mg of AT-G3 at 37° C. for 1 hour followed by standing at 4° C. for 12 hours. The mixture was then centrifuged at 12,000 g for 10 min. Quantities of 0.1 ml of the corresponding supernatants were intradermally injected into the recipient Guinea pigs. Four hours later, the animals were injected intravenously with AT-ND extract as mentioned above. The reduction in PCA titer of AT-ND antibody due to the pretreatment with AT-G3 fraction was taken to represent the relative measure of the common antigens shared between the AT-G3 fraction used for neutralization of PCA activity of AT-ND antibodies and the antigen (AT-ND) used for challenging the animals.

The results of these PCA studies are shown in Table V. Animals injected with untreated anti-AT-ND and anti-AT-G3, when challenged with AT-ND extract gave strong PCA titers of 2048 and 1024, respectively. However, absorption of anti-AT-ND serum with AT-G3 fraction reduced the PCA activity of AT-ND antibody (PCA titer from 2048 to 256 about 76% reduction) when challenged with AT-ND extract. These results indicate that AT-ND appears to have a few antigenic determinants which are common to AT-G3 fraction.

Example B6—Isolation and Properties of Hormodendrum Fraction

Fifty grams of Hormodendrum powder were processed as in Ex. A1 and become 44 g of defatted material which on extraction, ultrafiltration of the extract (H-CE) and dialysis yielded 1.27 g of water-soluble non-dialyzable material (H-ND). A portion of this H-ND water-soluble material was gel filtered as in Ex. A1, eluted and tubes combined into five fractions HG1–HG5 on the basis of 280 nm absorption, carbohydrate analysis and immunodiffusion tests with an antiserum to Hormodendrum crude extract (H-CE).

A fraction HG4 (constituting about one third of the total gel filtered eluted material) which eluted between the position of the standard proteins bovine serum albumin (BSA-MW 68,000) and carbonic anhydrase (CA-MW 30,000), showed, in tests outlined in Ex. B1-B5, antigenic and immunogenic properties including potency in RAST tests but did not give a passive cutaneous anaphylaxis (PCA) reaction, i.e was non-allergenic. The MW of this antigenic, non-allergenic fraction is seen to be above that of the equivalent fraction from A. tenuis.

We claim:

1. A method of decreasing or preventing allergic reactions in animals allergic to molds comprising:
administering parenterally to an animal allergic to molds, in an amount sufficient to decrease or prevent susceptibility of said animal to mold allergens, a protein- and carbohydrate-containing antigenic fraction extracted from mold causing such allergic reactions,
said fraction being characterized by being non-allergenic, and being obtained by steps comprising:
(a) defatting allergenic mold solids,
(b) extracting the defatted solids with an aqueous solution of pH about 7–8,
(c) dialyzing the extract solution to remove solute of less than about 10,000 MW,
(d) fractionating the extract by the equivalent of gel filtration on a medium operative to fractionate in the MW range about 10,000–100,000, and
(e) recovering the fraction showing RAST potency and lacking allergenicity, and capable of inducing IgG antibodies with the proviso that when the mold used to derive said antigenic fraction is *Alternaria tenuis* said fraction is equivalent to the narrow subfraction G3D5 in FIG. 2C.

2. The method of claim 1 wherein the mold is selected from the group consisting of Alternaria, Hormodendrum, Helminthosporium, Aspergillus, and Penicillium.

3. The method of claim 1 wherein the mold comprises an Alternaria species.

4. The method of claim 1 wherein the mold comprises *Alternaria tenuis, Alternaria solani* or Homodendrum.

5. The method of claim 1 wherein antigenic fractions from an Alternaria species and from another mold genus whose antigenic fraction is non- or only weakly-cross-reactive with that from the Alternaria species, are both administered to give a more polyvalent protection.

6. The method of claim 1 wherein the administration is subcutaneously.

7. The method of claim 1 wherein at least one dose of an effective amount within the approximate range of about 0.02 up to about 20 micrograms of total protein per dose, is administered.

8. The method of claim 7 wherein a series of doses of increasing amounts each within said range, are administered over several days or weeks.

9. The method of claim 7 wherein a single dose is given for rush desensitization.

10. The method of claim 7 wherein the dosage is repeated at intervals to maintain the level of protection or immunity desired.

11. The method of claim 7 wherein the fraction administered has been obtained by an additional step of (f) the equivalent of ion exchange chromatography, and recovering the subfraction showing antigenicity but lacking allergenicity.

12. The method of claim 11 wherein the chromatographic substrate for (f) is of the type of DEAE-cellulose.

13. The method of claim 11 wherein the fraction administered has been additionally (g) dialyzed against water.

14. The method of claim 1 wherein the fraction is combined with a selected adjuvant before administration.

15. The method of claim 1 wherein the fraction is administered in isotonic saline.

Figure 1:
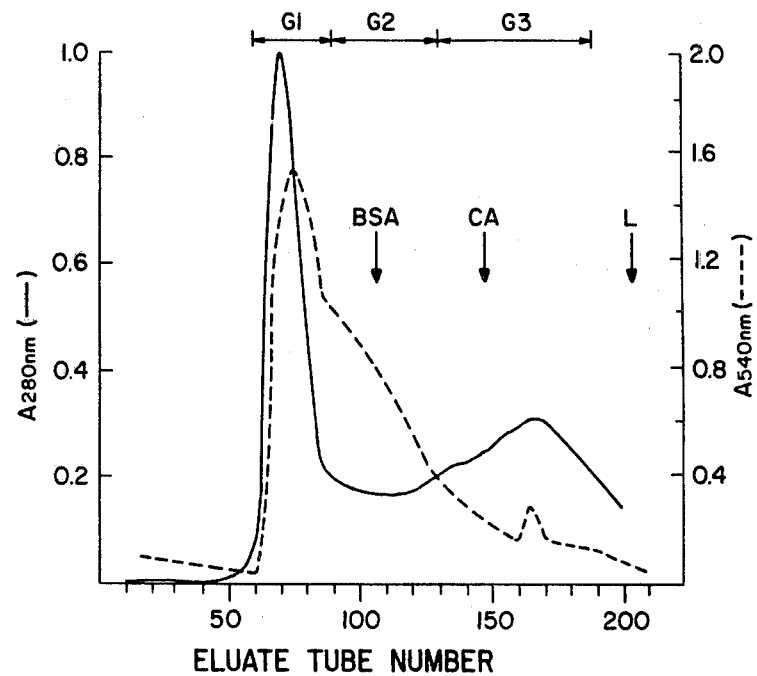
FIG. 1 is a graph plotting gel filtration eluate (successive tube number of 7 ml each) versus absorbance at 280 nm and carbohydrate content of *A. tenuis* non-dialyzable fraction (AT-ND) on Sephadex G-100. $A_{540}$ nm refers to readings in the carbohyrate assay. Tubes were pooled as indicated at G1, G2 and G3. The arrows indicate elution positions of the proteins used to calibrate the column, having serum albumin (BSA), carbonic anhydrase (CA) and lysozyme (L).

16. A protein- and carbohydrate-containing antigenic subfraction isolated from Alternaria mold causing allergic reactions, characterized by being non-allergenic, having a molecular weight of the order of about 25,000, and being obtained by steps comprising:
(a) defatting Alternaria mold solids;
(b) extracting the defatted solids with an aqueous solution of pH about 7–8,
(c) dialyzing the extract solution to remove solute of less than about 10,000 MW;
(d) fractionating the extract by the equivalent of gel filtration on a medium operative to fractionate in the MW range 10,000–50,000;
(e) recovering the fraction encompassing the equivalent of the G3 region in FIG. 1; and
(f) subjecting said recovered fraction from (e) to subfractionation by ion exchange chromatography, and recovering the non-allergenic, antigenic subfraction encompassing the equivalent of the G3D5 region in FIG. 2C.

17. A protein- and carbohydrate-containing antigenic fraction isolated from Hormodendrum mold causing allergic reactions, characterized by being non-allergenic and obtained by steps comprising:
(a) defatting Hormodendrum mold solids;
(b) extracting the defatted solids with an aqueous solution of pH about 7–8;
(c) dialyzing the extract solution to remove solute of less than about 10,000 MW;
(d) fractionating the extract by the equivalent of gel filtration on a medium operative to fractionate in the MW range about 10,000–100,000; and
(e) recovering the fraction eluting between bovine serum albumin MW 68,000 and carbonic anhydrase MW 30,000 which has antigenic and immunogenic properties including RAST potency and is lacking in allergenicity.

18. A pharmaceutical composition, giving polyvalent protection against allergic reactions in animals allergic to molds, comprising at least two antigenic fractions isolated from different allergy-causing molds and which are substantially non-cross-reactive, each fraction being characterized by being non-allergenic, and being obtained by steps comprising:
(a) defatting allergenic mold solids;
(b) extracting the defatted solids with an aqueous solution of pH about 7–8;
(c) dialyzing the extract solution to remove solute of less than about 10,000 MW;
(d) fractionating the extract by the equivalent of gel filtration on a medium operative to fractionate in the MW range about 10,000–100,000; and
(e) recovering the fraction showing RAST potency but lacking allergenicity, and capable of inducing IgG antibodies.

19. The pharmaceutical composition of claim 18 comprising the antigenic, non-allergenic fraction from an Alternaria mold and the similar fraction from a Hormodendrum mold.

20. The pharmaceutical composition of claim 18 comprising the antigenic, non-allergenic fraction from an Alternaria mold and the similar fraction from a Helminthosporium mold.

21. The pharmaceutical composition of claim 18 comprising the antigenic, non-allergenic fraction from *Alternaria tenuis* and the similar fraction from Hormodendrum.

* * * * *